United States Patent [19]

Chapman

[11] 4,311,866
[45] Jan. 19, 1982

[54] SEPARATION OF PRODUCTS OF HF ALKYLATION

[75] Inventor: Charles C. Chapman, Bartlesville, Okla.

[73] Assignee: Phillips Petroleum Company, Bartlesville, Okla.

[21] Appl. No.: 73,468

[22] Filed: Sep. 7, 1979

[51] Int. Cl.³ .............................. C07C 2/56; C07C 2/58
[52] U.S. Cl. ...................................... 585/719; 585/723
[58] Field of Search ................................. 585/719, 723

[56] References Cited

U.S. PATENT DOCUMENTS

| | | | |
|---|---|---|---|
| 2,412,726 | 12/1946 | Frey | 585/712 |
| 2,906,796 | 9/1959 | Putney | 585/302 |
| 2,910,521 | 10/1959 | Cobb | 585/701 |
| 3,763,022 | 10/1973 | Chapman | 585/719 |
| 3,857,904 | 12/1974 | Chapman | 585/719 |
| 3,919,342 | 11/1975 | Chapman | 585/703 |
| 3,925,501 | 12/1975 | Putney et al. | 585/715 |
| 3,929,924 | 12/1975 | Chapman | 585/703 |
| 3,957,901 | 5/1976 | Chapman | 585/701 |
| 4,112,010 | 9/1978 | Dixon | 585/719 |
| 4,115,471 | 9/1978 | Kesler | 585/719 |

*Primary Examiner*—Curtis R. Davis

[57] ABSTRACT

The reactor effluent hydrocarbon phase from an alkylation zone in which isoparaffin and olefin are contacted in the presence of HF catalyst to form alkylate product is treated by (1) separating a hydrocarbon phase from the reaction effluent; (2) separating the hydrocarbon phase in a first fractionator to produce a bottoms stream containing isoparaffin and alkylate; (3) flashing this bottoms stream to produce a flashed vapor enriched in isoparaffin and a flashed liquid enriched in alkylate; (4) subjecting this flashed liquid to a high pressure, high temperature fractionation in a second fractionator to produce isoparaffin overhead and alkylate from the kettle; and (5) passing the isoparaffin overhead as heat exchange fluid to at least one of (a) the indirect reboiling of the first fractionator kettle, (b) the indirect heating of the bottoms stream being fed from the first fractionator to the flashing step and (c) the indirect heating of the flashed liquid being fed to the second fractionator. In another embodiment, the hydrocarbon phase separated from the reaction effluent is further separated in a first fractionator to produce an overhead stream containing isoparaffin, alkane, HF, and organic fluoride impurities. This overhead stream is condensed and contacted with HF to remove the organic fluorides with the HF containing organic fluorides recycled to the reaction zone.

8 Claims, 1 Drawing Figure

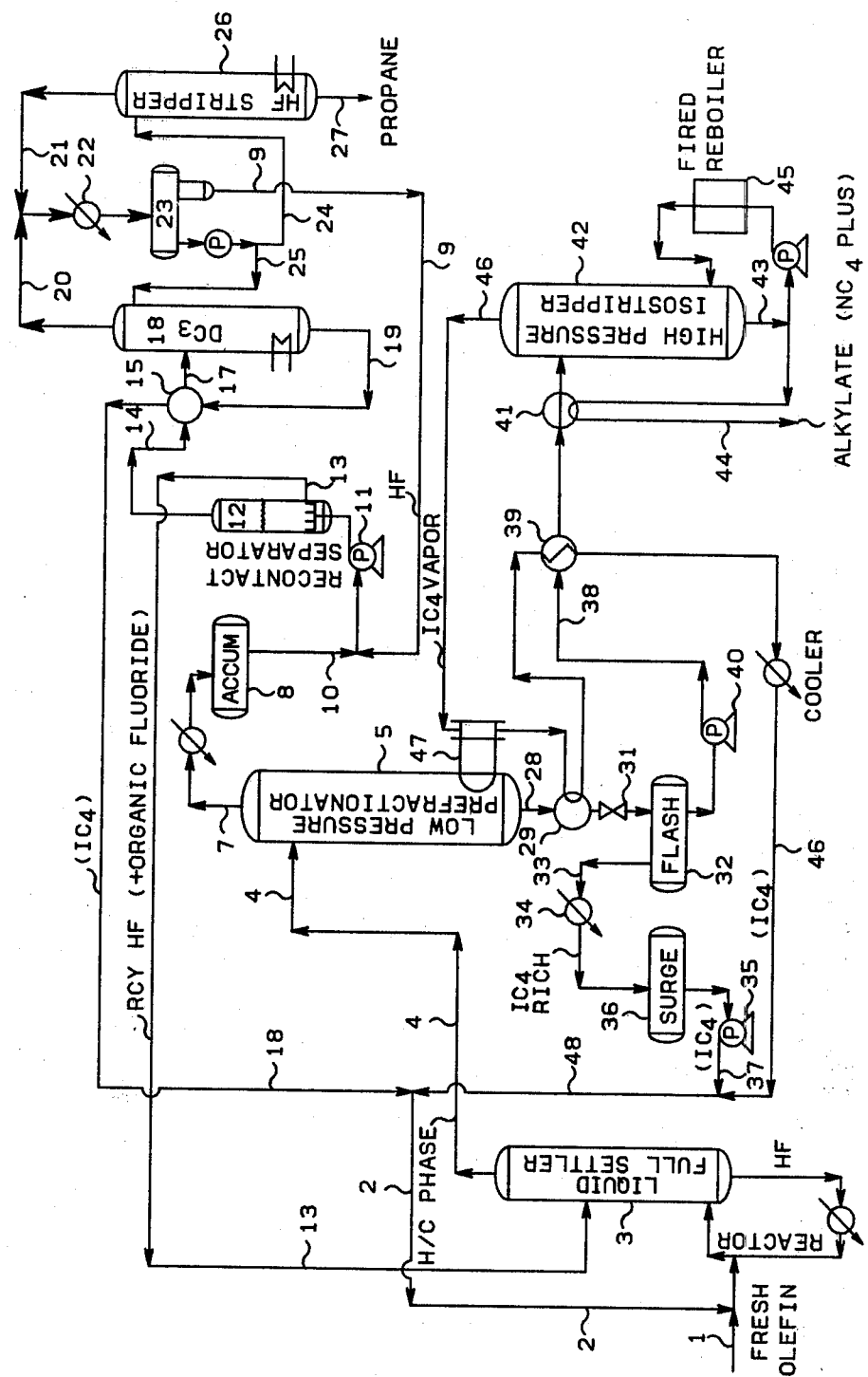

SEPARATION OF PRODUCTS OF HF ALKYLATION

BACKGROUND OF THE INVENTION

This invention relates to the reaction and recovery of products in a hydrogen fluoride (HF) catalyzed alkylation. In one of its aspects, this invention relates to the contact of isoparaffin with olefin in the presence of HF catalyst to produce alkylate product. In another of its aspects, this invention relates to the supplying of energy for the separation of the reaction products of an alkylation process.

Various schemes have been proposed to maximize the efficiency of energy use in the separation of the components of the effluent from various chemical reactions. Some reactions, such as the contact of isoparaffin with olefin in the presence of an HF catalyst to produce an alkylate product, produce an effluent that contains a variety of components that can be profitably separated as salable product or for recycle into the reaction process. Since the reaction effluent also contains impurities which can be harmful to the salability of the product or to the efficiency of the reaction the removal of these impurities also becomes an important factor to consider in the treatment of the reaction effluent. Effluent treatment is a multi-faceted problem which lends itself to a variety of solutions.

In the present invention use is made of a flashing operation to reduce the load of low boiling fraction from the kettle of a first fractionator that is passed to a second high pressure, high temperature fractionator. This operation allows the use of a smaller second fractionator, i.e., less trays in the fractionator. For further energy and equipment economies the hot overhead from the high pressure, high temperature fractionator can be passed into indirect heat exchange with the bottoms fraction leaving the first fractionator to increase the temperature of the stream before it is flashed thereby causing more of the low boiling material to flash and even less material to be passed as feed to the high pressure, high temperature fractionator.

It is therefore an object of this invention to provide a method for separating isoparaffin from the hydrocarbon phase of an alkylation reactor effluent which economizes both in equipment and energy usage. It is another object of this invention to provide a system for heat exchanging product and feed streams in a recovery system utilizing two fractionation columns in series to provide a system in which less material needs to be treated in the second fractionator. It is still another object of this invention to provide a method for treating the overhead from a fractionator containing isoparaffin, HF, and organic fluoride impurities so that the organic impurities are removed.

Other aspects, objects and the various advantages of this invention will become apparent upon reading this specification and the appended claims.

STATEMENT OF THE INVENTION

According to this invention a process is provided for treating the reactor effluent hydrocarbon phase from an alkylation zone in which isoparaffin and olefin are contacted in the presence of HF catalyst to form alkylate product. In the process (1) a hydrocarbon phase is separated from the reaction effluent; (2) this hydrocarbon phase is then separated in a fractionator to produce an HF-free bottoms stream containing isoparaffin, alkylate, and essentially no propane, and an overhead stream containing isoparaffin, propane and HF; (3) this bottoms stream is flashed to produce a first flashed vapor enriched in isoparaffin and a first flashed liquid enriched in alkylate as compared to the bottoms stream before flashing; and (4) flashed liquid is subjected to a high pressure, high temperature fractionation in a second fractionator to produce isoparaffin overhead and alkylate from the kettle. Preferably, the isoparaffin overhead is then passed as heat exchange fluid to at least one of (a) the indirect reboiling of the first fractionator kettle, (b) the indirect heating of the bottoms stream being fed from the first fractionator to the flashing operation and (c) the indirect heating of flashed liquid being fed to the second fractionator. In the most preferred operation the isoparaffin overhead is passed at least as heat exchange fluid for indirectly heating the bottoms stream being fed from the first fractionator to the flashing operation.

In another embodiment of the invention the hydrocarbon phase separated from the reaction effluent is further treated by (1) separating the hydrocarbon phase in a first fractionator to produce a first fractionator overhead stream containing isoparaffin, alkane, HF, and organic fluoride impurities; (2) condensing this first fractionator overhead stream; and (3) contacting the condensed first fractionator overhead stream with HF to remove organic fluorides. In a preferred embodiment, the HF stream containing organic fluorides is circulated to the reaction zone.

The invention can best be understood in conjunction with the drawing which is a schematic representation of a process according to this invention.

Referring now to the drawing, fresh olefin and isoparaffin, which for the sake of this illustration are isobutane and butylene, respectively, are charged through line 1 along with recycle isobutane from line 2 into an alkylation zone along with HF catalyst. Reaction conditions well known in the art are maintained in the reactor so that an alkylate product is produced. Effluent from the reactor flows into a liquid full settler 3 in which hydrogen fluoride settles and is circulated through a cooler and into fresh contact with the olefin and isoparaffin feedstock.

A hydrocarbon phase containing alkylate, isobutylene, propane, HF, and organic fluoride impurities is pressured through line 4 and to a first fractionator 5 which can be denominated a low pressure prefractionator. From this fractionator is produced an overhead stream containing isobutane, propane, HF, and organic fluoride impurity and a bottoms stream containing isobutane and alkylate.

The overhead stream from low pressure prefractionator 5 passes through line 7 and a cooler to be condensed into accumulator 8 from which it is passed through line 10 and joined by HF from line 9 to be passed into the suction of a pump 11 and into a recontact separator 12. This contacting of the condensed overhead stream with HF effectively removes organic fluorides from solution in the isobutane into solution in the HF. In recontact separator 12, the isobutane and HF separate with the HF which contains organic fluoride impurities passed through line 13 back to the liquid full settler 3 where reaction conditions are sufficient to effectively alkylate isobutane with the organic fluoride contaminant.

Hydrocarbon effluent from the recontact separator 12 passes through line 14, heat exchanger 15 and line 17 into depropanizer column 18. The remainder of the operation is well known in the art and consists of fractionating hydrocarbon feedstock from line 17 to produce a bottoms stream 19 that is essentially isobutane and an overhead stream 20 which contains essentially only propane and HF. The overhead 20 is passed through condenser 22 and collected in accumulator 23 from which a portion is passed through line 25, as reflux, back to depropanizer column 18 and the remainder is passed through line 24 as feed for the HF stripper 26.

In the HF stripper 26 a separation is made to produce a bottoms stream 27 that is essentially propane and an overhead stream 21 containing essentially only propane and HF which is passed through condenser 22 and collected as condensate in accumulator 23. On the accumulator 23 is a separation leg in which relatively pure HF collects to be passed through line 9 back into contact with stream 10 which is contaminated with organic fluoride.

The HF-free bottoms stream 28 containing isobutane and alkylate is passed from low pressure prefractionator 5 through a pressure regulator 31 into flash tank 32 where a flashed vapor enriched in isobutane and a flashed liquid enriched in alkylate, as compared to the flash tank feed, are produced. Preferably the bottoms stream 28 is passed through heat exchanger 29 to be heated before being flashed so that the flashed vapor is even more enriched with isobutane and flashed liquid is even more enriched with alkylate. The flashed vapor is passed through line 33, condenser 34 and surge tank 36 and to the suction of pump 35 from which it is pumped through line 37 to join other recycle isobutane streams to return to the reactor.

The flashed liquid from tank 32 is passed to pump 40 to be pumped through line 38 into a second fractionator 42 which can be denominated a high pressure, high temperature isostripper. From the second fractionator is produced an overhead stream which is hot isobutane vapor and a kettle stream which is alkylate product, i.e., n-butane and heavy hydrocarbons.

The hot isobutane vapor which is the overhead product from the isostripper is passed through line 46 to be heat exchanged in a preferred embodiment of this invention with at least one of (a) the first fractionator kettle liquid in reboiler 47, (b) the bottoms liquid being passed from the first fractionator to the flashing step as this liquid passes through heat exchanger 29, and (c) the flashed liquid being fed to the high pressure, high temperature isostripper as it passes through heat exchanger 39. In the most preferred embodiment, the hot isobutane vapor is indirectly heat exchanged with at least the bottoms liquid from the first fractionator in heat exchanger 29. In this process there is sufficient heat in the overhead vapor to allow exchange with all the above-named streams and still require additional cooling as the stream is passed via 46 into contact with other recycled isobutane streams to be returned to the reaction zone.

The bottoms stream from the high pressure isostripper 42 is passed through line 43 with a portion being pumped through a fired reboiler 45 to provide sufficient energy for the separation operation in the isostripper. The remainder or yield portion of the hot bottoms stream can be passed through heat exchanger 41 where it is indirectly heat exchanged with the feed liquid passed from the flash tank to the isostripper. Alkylate product is removed through line 44.

Set out below are calculated values for operating conditions and flows for the typical operation of the system as described above with heat exchange of the high pressure, high temperature isostripper overhead with each of (1) the first fractionator kettle liquid (2) the first fractionator bottoms feed to the flash operation, and (3) the flashed liquid feed to the high pressure, high temperature isostripper.

| OPERATING CONDITION AND FLOWS (Calculated) | |
|---|---|
| A. Operating Conditions: | |
| HF Alkylation Reactor: | |
| Pressure, psia., | 150 |
| Temperature, °F., | 90 |
| HF/Total H/C Vol. Ratio, | 4:1 |
| IC$_4$ (total)/Olefin Vol. Ratio, | 20:1 |
| Prefractionator 5: | |
| Pressure, psia, | 130 |
| Temperature, °F., | |
| Top, | 125 |
| Bottom, | 150 |
| Accumulator 8: | |
| Pressure, psia., | 115 |
| Temperature, °F., | 100 |
| Separator 12: | |
| Pressure, psia., | 270 |
| Temperature, °F., | 100 |
| Depropanizer 18: | |
| Pressure, psia., | 255 |
| Temperature, °F., | |
| Top, | 120 |
| Bottom, | 200 |
| HF Stripper 26: | |
| Pressure, psia., | 300 |
| Temperature, °F., | |
| Top, | 130 |
| Bottom, | 139 |
| Isostripper 42: | |
| Pressure, psia., | 245 |
| Temperature, °F., | |
| Top, | 207 |
| Bottom, | 416 |
| Flash 32: | |
| Pressure, psia., | 85 |
| Temperature, °F., | 113 |
| Surge 36: | |
| Pressure, psia., | 75 |
| Temperature, °F., | 100 |
| B. Flow Rates: (B/D = Barrels/Day) | |
| (1) Feed Isobutane and Olefin, B/D | 13,032 |
| Vol. % Butylenes, | 43 |
| Vol. % Isobutane, | 50 |
| Vol. % Propane, | 3 |
| Vol. % N-Butane | 4 |
| (2) Total Recycle Isobutane, B/D | 112,180 |
| Vol. % Isobutane | 94 |
| Feed to Prefractionator, B/D | 124,710 |
| Vol. % Propane | 1.3 |
| Vol. % Isobutane | 85.4 |
| Vol. % Normal Butane | 3.5 |
| Vol. % IC$_5$ Plus | 9.2 |
| Vol. % HF | 0.6 |
| (9) HF, B/D | 120 |
| Feed to Pump (11), B/D | 14,826 |
| Vol. % Propane, | 3.5 |
| Vol. %. Isobutane | 88.8 |
| Vol. % NC$_4$ | 2.5 |
| Vol. % IC$_5$ Plus | 0.3 |
| Vol. % HF | 4.9 |
| Feed Feed to Depropanizer (18), B/D | 14,226 |
| Vol. % Propane, | 3.7 |
| Vol. % Isobutane | 92.6 |
| Vol. % NC$_4$ | 2.6 |
| Vol. % IC$_5$ Plus | 0.3 |
| Vol. % HF | 0.8 |
| (27) LPG Yield, B/D | 356 |
| Vol. % C$_3$, | 98.6 |
| Vol. % IC$_4$ | 1.4 |
| Vol. % HF | nil |

-continued

| OPERATING CONDITION AND FLOWS (Calculated) | |
|---|---|
| (28) To Flash 32, B/D | 109,884 |
| Vol. % C$_3$ | 0.9 |
| Vol. % iC$_4$, | 85.1 |
| Vol. % nC$_4$, | 3.6 |
| Vol. % iC$_5$ Plus, | 10.4 |
| Vol. % HF, | nil |
| (37) Isobutane from Flash 32, B/D | 32,727 |
| Vol. % C$_3$, | 1.8 |
| Vol. % iC$_4$, | 94.6 |
| Vol. % nC$_4$, | 3.6 |
| Vol. % HF, | nil |
| (38) Feed to Isostripper 42, B/D, | 77,150 |
| Vol. % C$_3$, | 0.6 |
| Vol. % iC$_4$, | 80.5 |
| Vol. % nC$_4$, | 3.9 |
| Vol. % iC$_5$ Plus, | 14.5 |
| Vol. % HF, | nil |
| (44) Alkylate Yield (iC$_5$ Plus, B/D | 10,115 |
| RON, Clear, | 98.0 |
| (46) Isobutane Vapor (B/D as liquid), | 66,494 |
| Temperature, °F., | 207 |
| Vol. % C$_3$, | 0.7 |
| Vol. % iC$_4$, | 93.8 |
| Vol. % nC$_4$, | 3.8 |
| Vol. % iC$_5$ Plus, | 1.7 |
| Vol. % HF, | nil |

Using the operating conditions and flow rates as calculated above the advantages of operating the recovery system by flashing the bottoms stream from the first fractionation column can be stated as follows: about 35% of the isobutane in the low pressure prefractionator bottoms is flashed to vapor in the flash operation thereby decreasing the feed to the high pressure, high temperature isostripper, which allows operation of the isostripper with about 40% less reboiler duty than would be required for operation without the flashing; since the isostripper is operated at a relatively high pressure which is permitted by the pumping of a liquid stream from the flash operation the hot vapor produced overhead from the isostripper can furnish all of the heat necessary to reboil the low pressure prefractionator eliminating the use of steam for this purpose; and the prefractionator column itself can be reduced in size requiring only 15 trays as compared to 35 trays necessary for the separation without the flash operation.

Although the process above has been described with an isoparaffin feed of isobutane and an olefin feed of butylene, it should be evident to those skilled in the art that this process is adaptable to alkylations using any combination of isoparaffin and olefin that can be alkylated in the presence of HF catalyst.

I claim:

1. A process for treating the reactor effluent hydrocarbon phase from an alkylation zone in which isoparaffin and olefin are contacted in the presence of HF catalyst to form alkylate product, said method comprising:
   (a) separating hydrocarbon phase from the reaction effluent;
   (b) separating said hydrocarbon phase in a first fractionator to produce an HF-free bottoms stream comprising isoparaffin and alkylate; and
   (c) flashing said bottoms stream to produce a flashed vapor enriched in isoparaffin and a flashed liquid enriched in alkylate as compared to said bottoms stream.

2. A method of claim 1 wherein said flashed liquid is subjected to a high pressure, high temperature fractionation in a second fractionator to produce isoparaffin overhead and alkylate from the kettle, and
   the isoparaffin overhead is passed as heat exchange fluid to at least one of (a) indirectly reboiling the first fractionator kettle, (b) indirectly heating the bottoms stream being fed from the first fractionator to the flashing operation, and (c) indirectly heating flashed liquid being fed to said second fractionator.

3. A method of claim 2 wherein the isoparaffin overhead is passed as heat exchange fluid at least for indirectly heating the bottoms stream being fed from the first fractionator to the flashing operation.

4. A method of claim 1 wherein said flashed vapors are condensed and recirculated to the reaction zone.

5. A method of claim 2 wherein said isoparaffin overhead after passing as heat exchange fluid is further condensed and recycled to the reaction zone.

6. A method of claim 2 wherein said alkylate from the kettle of the second fractionator is indirectly heat exchanged with the flashed liquid rich in alkylate before said flashed liquid is subjected to fractionation in said second fractionator.

7. A process for treating the reactor effluent hydrocarbon phase from an alkylation zone in which isoparaffin and olefin are contacted in the presence of HF catalyst to form alkylate products, said method comprising:
   (a) separating a hydrocarbon phase from the reaction effluent;
   (b) separating said hydrocarbon phase in a first fractionator to produce a first fractionator overhead stream comprising isoparaffin, alkane, HF, and organic fluoride impurity;
   (c) condensing said first fractionator overhead stream;
   (d) contacting said condensed first fractionator overhead stream with HF to remove organic fluorides; and
   (e) circulating HF which contains organic fluorides to said reaction zone.

8. A process of claim 7 wherein (f) said first fractionator overhead stream, after contact with HF, is subjected to depropanizing fractionation.

* * * * *